United States Patent [19]

Bisera et al.

[11] Patent Number: 4,638,811
[45] Date of Patent: Jan. 27, 1987

[54] VASCULAR INTERFACE

[75] Inventors: Jose Bisera, Camarillo; James H. Carrington, Los Angeles; Max H. Weil, Beverly Hills, all of Calif.

[73] Assignee: Institute of Critical Care Medicine, Los Angeles, Calif.

[21] Appl. No.: 216,189

[22] Filed: Dec. 15, 1980

Related U.S. Application Data

[63] Continuation of Ser. No. 830,847, Sep. 6, 1977, Pat. No. 4,258,717.

[51] Int. Cl.⁴ .................. A61B 5/00; A61M 35/00; A61M 5/00
[52] U.S. Cl. ............................ 128/673; 604/4; 604/9; 604/21
[58] Field of Search ........... 128/1 R, 632, 635, 214 R, 128/214 B, 213 R, 213 A, 247, 673; 604/4, 9, 21

[56] References Cited

U.S. PATENT DOCUMENTS 3,838,682  10/1974  Clark et al. ............ 128/214 B
3,859,985  1/1975  Eckhart ................... 128/214 B Primary Examiner—John F. Terapane
Assistant Examiner—T. J. Wallen
Attorney, Agent, or Firm—Freilich, Hornbaker, Rosen & Fernandez

[57] ABSTRACT

Apparatus for facilitating the performance of medical procedures involving the vascular system of a patient, especially in a critical care environment, such as withdrawal of blood for analysis and infusion of medication. In the taking of a blood sample, blood flows through an arterial catheter connected to an artery of the patient, past a sample station, and then through a venous catheter that brings the blood back to the patient, the various mechanisms being connected by transparent plastic tubes. After a sample is taken, the tubes are flushed through the sample station, arterial catheter, and the venous catheter. Calibration of all pressure transducers requires application of high and low pressures to them, the high pressure being obtained by applying a high pressure (e.g. 200 mm Hg) to a bottle of saline solution which is also utilized to flush the tubes and which is connected to all of the transducers.

5 Claims, 10 Drawing Figures

SAMPLE (ARTERIAL SAMPLE, STEP #2)

FLUSH-1 (ARTERIAL SAMPLE STEP #3)

FLUSH-2 (ARTERIAL SAMPLE STEP #4)

CALIBRATION

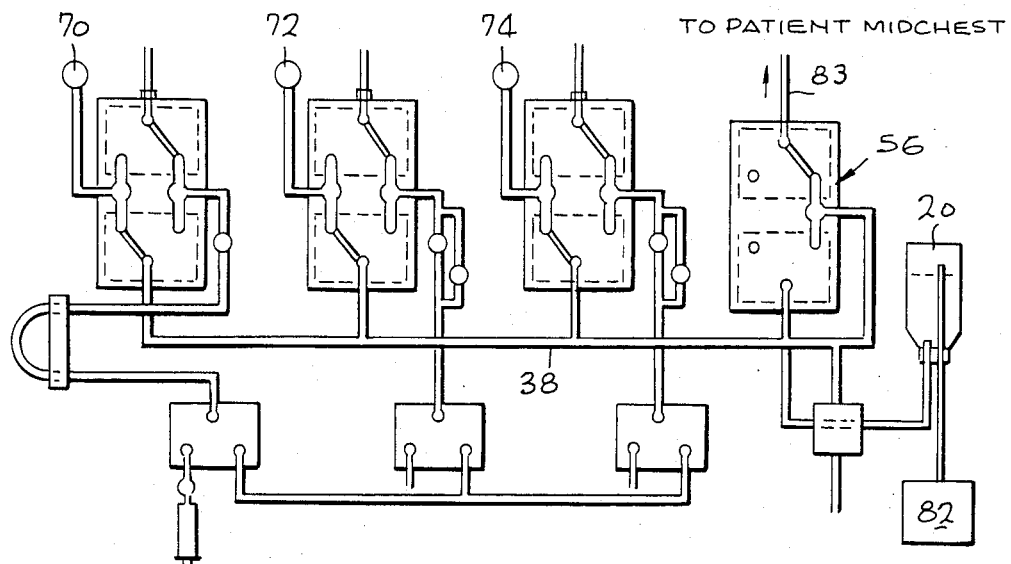
FIG. 8
CALIBRATION TO PATIENT
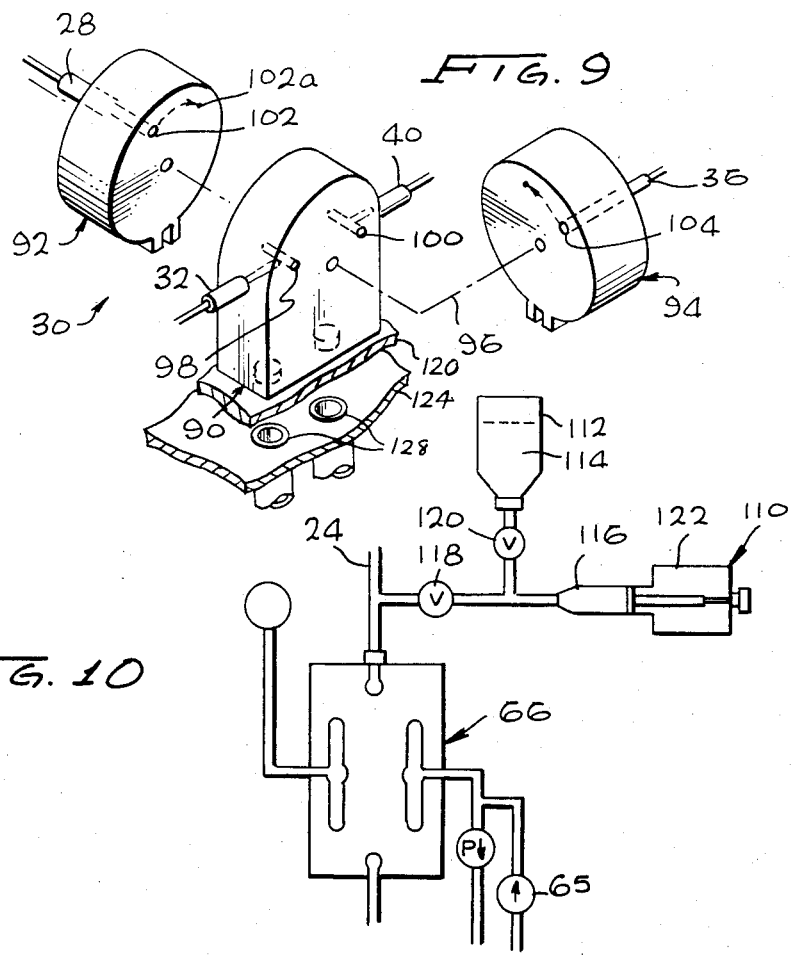
FIG. 9
FIG. 10

VASCULAR INTERFACE

CROSS-REFERENCE TO RELATED APPLICATIONS

This is a continuation application of application Ser. No. 830,847 filed Sept. 6, 1977 now U.S. Pat. No. 4,258,717 issued Mar. 31, 1981.

BACKGROUND OF THE INVENTION

This invention relates to apparatus for performing procedures involving the vascular system of a patient.

The vascular system of a patient in a critical care environment is often monitored by the long-term connection of catheters to an artery and to a vein, and often also to the pulmonary artery of the patient. When a procedure is performed, such as the taking of a blood sample, a nurse must operate many stopcocks in proper sequence, to withdraw saline solution lying in the catheter for disposal, to continue the withdrawal until blood flows out, to operate a syringe to take the blood sample, to disconnect the syringe and connect a bottle of saline solution to flush the catheter with saline solution back to the patient, and then to maintain a small or occasional flow of saline solution to maintain patency (unclogged condition) of the catheter. Because of the numerous stopcocks that must be operated in proper sequence, there is a considerable possibility of error. Similar complications are encountered in performing other procedures, such as infusion of medicines and calibration of the pressure measuring system, and all of these procedures take appreciable time.

SUMMARY OF THE INVENTION

In accordance with one embodiment of the present invention, a vascular interface apparatus is provided which automates procedures involving coupling to the vascular system of a patient and the calibration of the apparatus. In one mode of operation, for taking a blood sample, valves are opened to connect an arterial catheter through tubes extending past a sample station and then to a venous catheter to carry the blood from the artery to the vein of a patient. After the tubes fill with blood, at least past the sample station, a syringe can be operated at the sample station to take a blood sample. Thus, saline solution in the tubes can be completely replaced by blood prior to taking the blood sample. Also, this is accomplished without wasting the blood, since it is returned to the vein. Flushing of the tubes is accomplished by first connecting a bottle of saline solution through tubes leading to the catheter to force saline through the tubes and catheter and into the patient, and then saline is flushed through tubes leading to the venous catheter and through that catheter to the patient. The various valves and pumps utilized in the procedure are automatically operated in proper sequence when a proper button is operated.

The novel features of the invention are set forth with particularity in the appended claims. The invention will best be understood from the following description when read in conjunction with the accompanying drawings.

BRIEF DESCRIPTION OF THE DRAWINGS

FIG. 8 is a view of the diagram of FIG. 7, shown during the second step in a calibration process.

FIG. 9 is a partial perspective exploded view of one of the valves of the apparatus of FIG. 1

FIG. 10 is a partial diagram of the apparatus of FIG. 2, showing the injecting station thereof.

DESCRIPTION OF THE PREFERRED EMBODIMENTS

Figure 1:
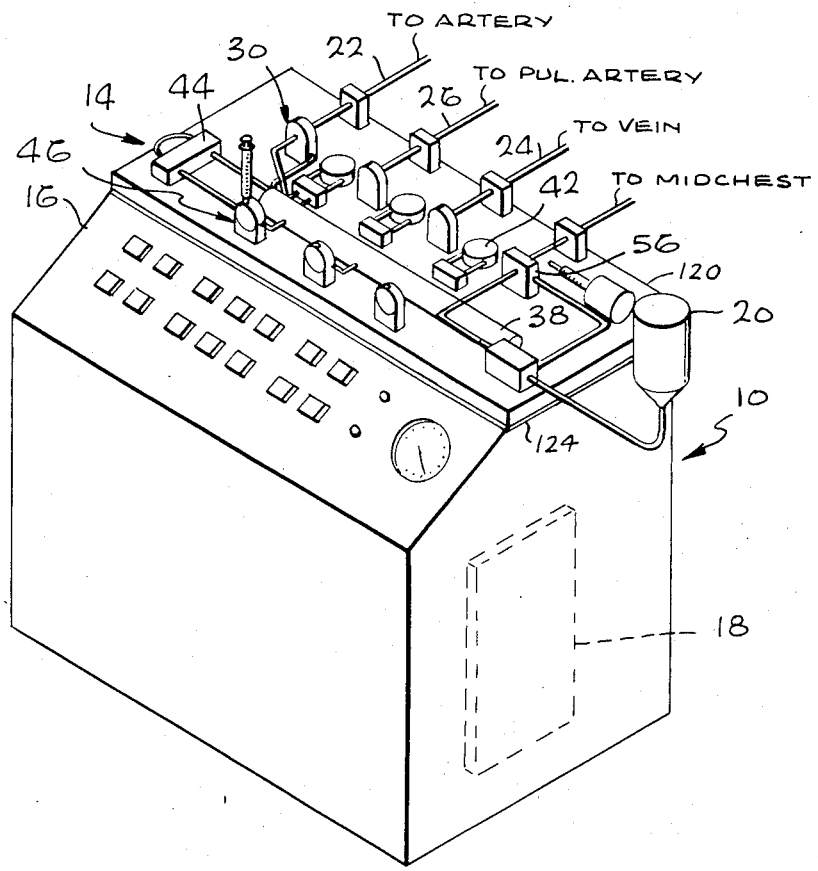
FIG. 1 is a perspective view of a vascular interface apparatus constructed in accordance with the present invention.

FIG. 1 illustrates a vascular interface apparatus 10 which includes a group of catheters 12 connected to a patient, and mechanisms for enabling the automatic performance of procedures involving the vascular system of the patient. The apparatus includes a valving portion 14 which actually controls the interior connection of the catheters to each other and to other devices, a control panel 16 which can be operated by a clinician to cause a resulting interconnection of various valves so as to perform any of a variety of procedures, and a circuitry portion 18 that operates the valves and other devices of the valving portion 14 in response to the operation of the controls on the control panel 16. A bottle 20 of normal saline solution is coupled to the valves of the valving portion 14 to supply saline solution which is extensively utilized in performing procedures.

Figure 2:
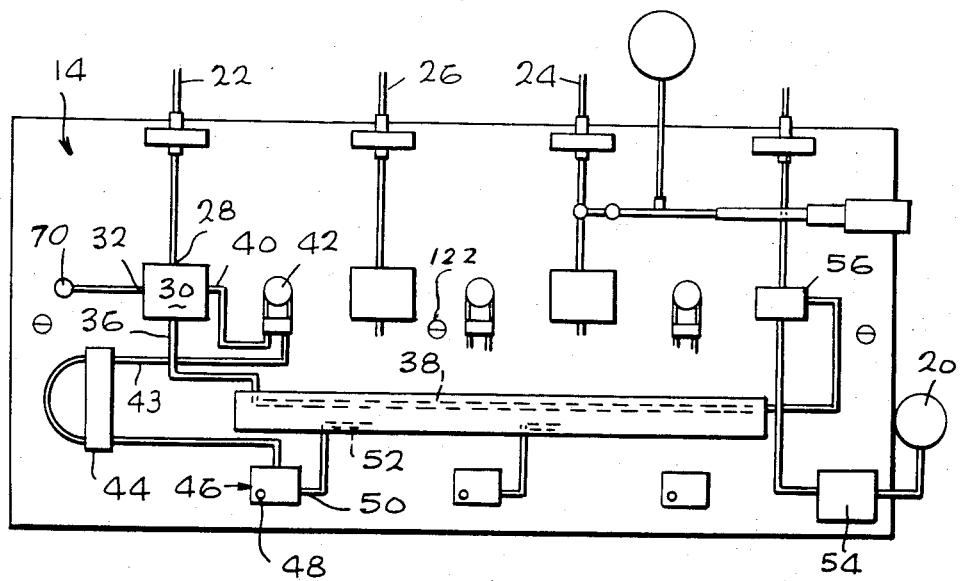
FIG. 2 is a plan view of the valve and conduit arrangement of the apparatus in FIG. 1.

FIG. 2 illustrates the arrangement of valves, pumps, and conduits of the valving portion 14 of the vascular interface apparatus. The valving portion includes an arterial catheter 22 normally connected to an artery of the patient, a venous catheter 24 normally connected to a vein of the patient, and a pulmonary artery catheter 26 which can be used for connection to the pulmonary artery of the patient. The arterial catheter 22 is coupled to one port 28 of an arterial interface valve 30. The valve 30 has a second port 32 connected to a pressure transducer 70, a third port 36 connected to a flush conduit or manifold 38, and a fourth port 40 connected to a peristaltic pump 42. The peristaltic pump 42 has an opposite end connected through an interface 44 to an arterial sampling valve 46. The valve 46 has one outlet 48 forming a syringe receiver for delivering a blood sample, and another outlet 50 that leads to a sample manifold 52.

The venous catheter 24 and pulmonary artery catheter 26 are connected to corresponding valve and pump arrangements similar to that which is coupled to the arterial catheter 22. In addition, the bottle of saline solution 20 is connected through a flush block 54 which is coupled through a flush valve 56 to the flush manifold 38.

Figure 3:
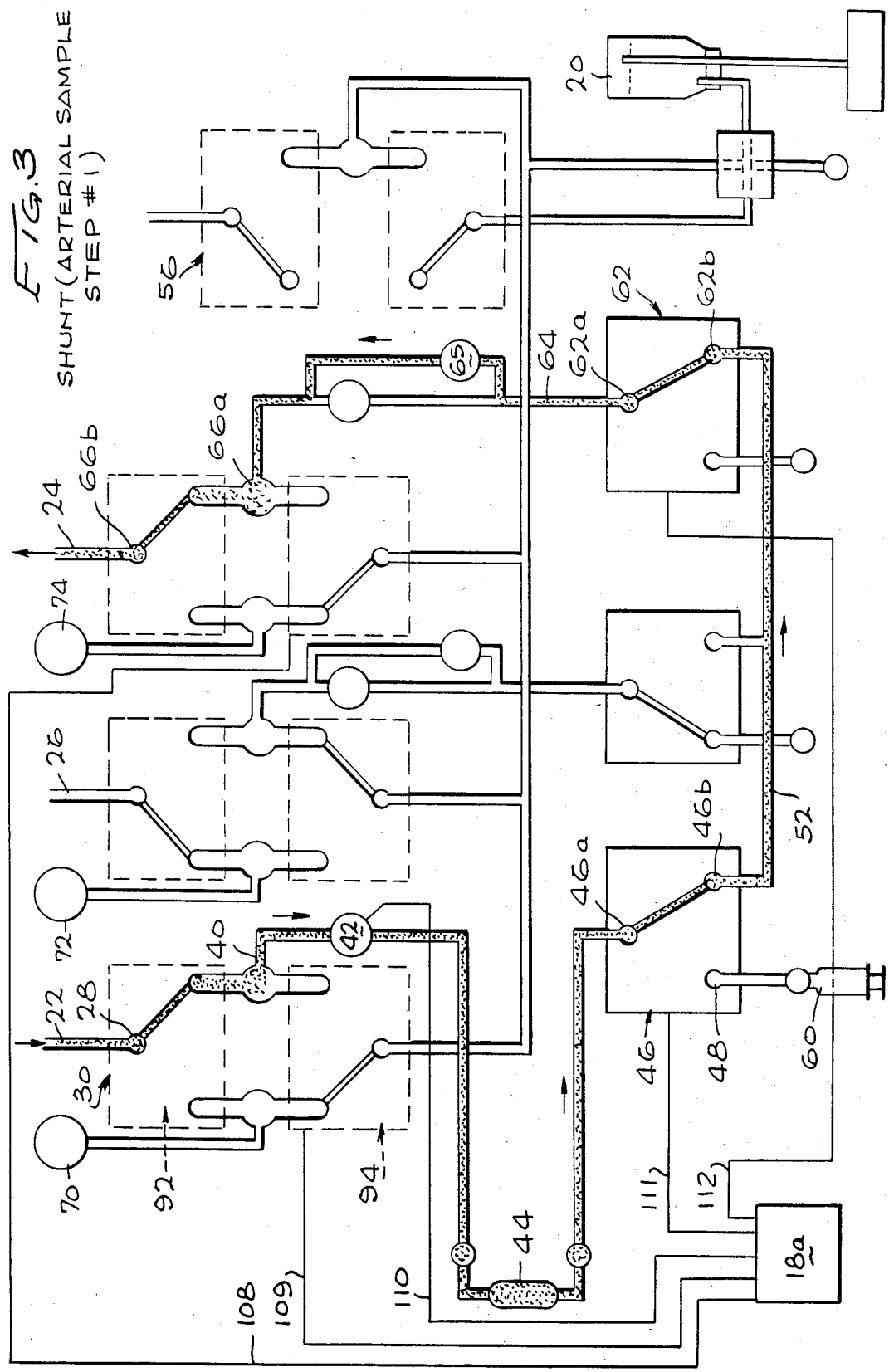
FIG. 3 is a diagram of the apparatus of FIG. 2, showing it set up for the first step in the taking of an arterial blood sample, this being a shunt step wherein blood is made to flow from the arterial catheter to the venous catheter, past an arterial sample station.

An understanding of the manner of operation of the apparatus can be best gained by reviewing the operation of a system for various procedures. FIGS. 3–6 illustrate four steps in utilization of the apparatus in the taking of an arterial sample, the sample ultimately being received in a sample syringe 60 that is connected to the sample port 48 of the arterial sample valve 46. The arterial interface valve 30 is first operated so that its catheter port 28 is connected to the pump port 40, and the pump 42 is operated. Accordingly, blood can flow from the artery of the patient and through the pump 42, and through a conduit 43 extending past the interface 44 and to the sampling valve 46. The sampling valve 46 is operated so that blood flowing in through port 46a passes out through a port 46b that leads to the sample manifold 52. The sample manifold serves as a conduit that is coupled to a port 62b of a venous sample valve 62. The venous sample valve 62 is operated so that another one of its ports 62a is connected to a conduit 64. The conduit 64 leads through a check valve 65 towards a port 66a of a venous interface valve 66. The venous interface valve 66 is operated so that it connects the port 66a to another port 66b that connects to the venous catheter 24. As a result of this interconnection and of operation of the pump 42, blood flows from the artery of the patient by way of the arterial catheter 22, past the arterial sample valve 46 and through the venous catheter 24 to the vein of a patient. The interconnections of FIG. 3 provide a "shunt" path, which clears the pathway of normal saline and replaces it with arterial blood. After a short period of time of blood flow blood is available at the arterial sampling valve 46 which is free of normal saline that was earlier present in all of the system.

Figure 4:
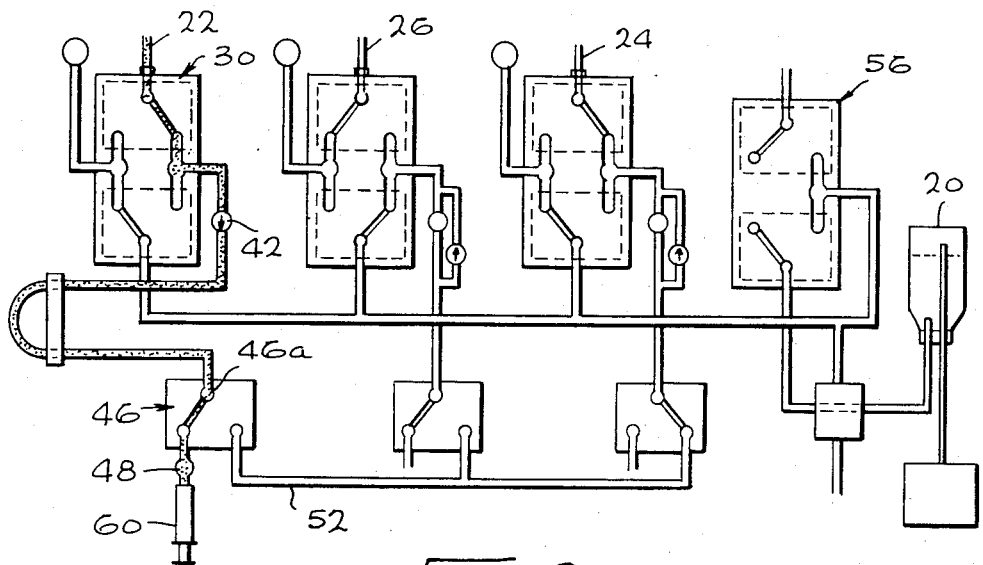
FIG. 4 is a view of the apparatus of FIG. 3, shown during a second step in the taking of an arterial sample, the step involving the transference of blood to a syringe.

FIG. 4 illustrates the system of FIG. 3 during a next step in the sampling procedure, during which a blood sample is received by the syringe 60. The valves are in the same condition as was in FIG. 3, except that the arterial sampling valve 46 is operated to connect the port 46a to the port 48, to which the syringe 60 is connected. The peristaltic pump 42 is operated sufficiently long to fill the syringe 60 with the required amount of blood. The pump then stops to cease fluid flow.

Figure 5:
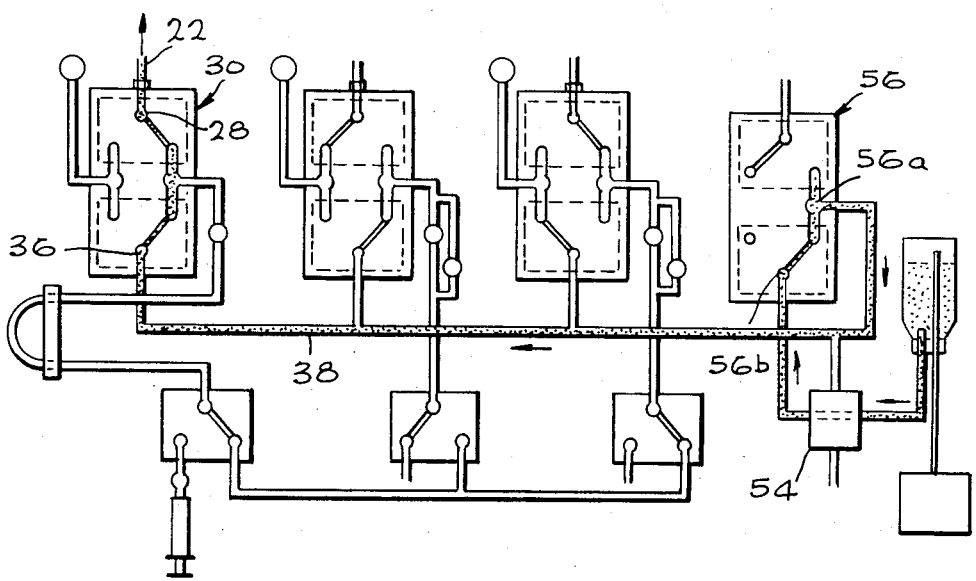
FIG. 5 is a view of the apparatus of FIG. 3, during a third step in the taking of an arterial sample, this being an arterial catheter flush procedure.

FIG. 5 illustrates a next step in the process, wherein the valves of the apparatus are set to flush the arterial catheter 22. This is accomplished by operating a flush valve 56 to interconnect its ports 56a and 56b so that saline solution flows from the bottle 20 of saline solution past the flush block 54 and through the valve 56 to the flush manifold 38. The fluid passes from the flush manifold 38 through the port 36 of the arterial interface valve 30, and through the port 28 leading to the arterial catheter, to flush the arterial catheter with saline solution all the way to the artery of the patient.

Figure 6:
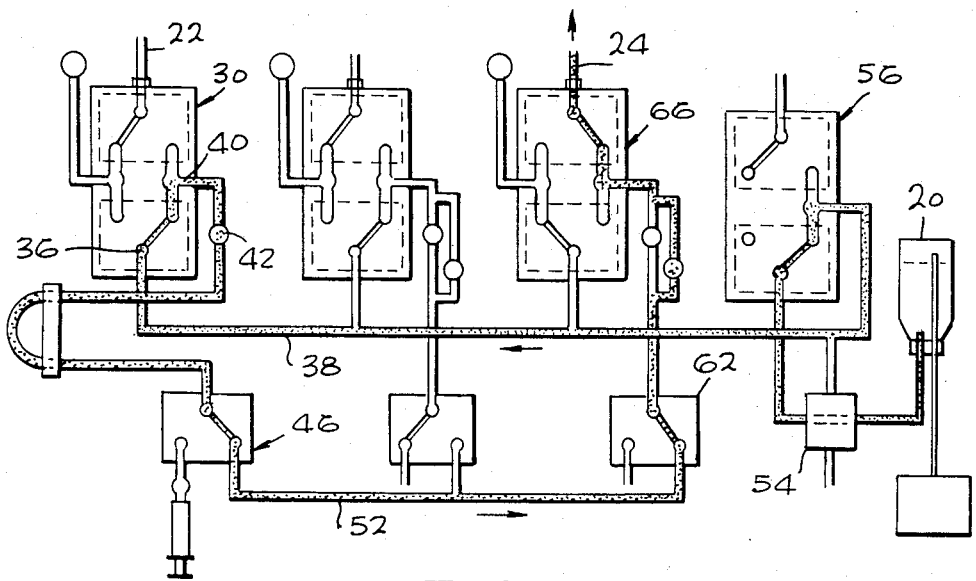
FIG. 6 is a view of the apparatus of FIG. 3, showing a fourth step in the taking of an arterial sample, this being a flush procedure which flushes the venous catheter and other tubes.

FIG. 6 illustrates a final step in the process, wherein the portion of the system leading from the port 40 of the arterial interface valve to the venous catheter 24 is flushed. This is accomplished by utilizing the system as connected in FIG. 5, but with the arterial interface valve 30 operated to interconnect its ports 36 and 40 and by operating the pump 42. This causes saline solution to pass from the flush manifold 38 through the pump 42, through the arterial sample valve 46, through the sample manifold 52, through the venous sample valve 62, through the venous interface valve 66, and through the venous catheter 24 leading to the patient. Of course, all of the interconnecting conduits are also flushed. By performing the two flush steps indicated in FIGS. 5 and 6, the entire portion of the system which was filled with blood, will have now been flushed with saline solution. All blood in the system which was not taken in the sample syringe, will have been returned to the patient, along with only a limited amount of saline.

The pulmonary artery catheter 26 and a corresponding pulmonary artery sample valve 68, are provided to enable the taking of samples from the pulmonary artery of a patient. This apparatus operates in the same manner as the general arterial interface valve 30 and sampling valve 46 that are used primarily in obtaining samples from the femoral artery.

FIG. 10 illustrates a portion of the vascular interface which includes an injection station 110 coupled to the venous catheter 24 to enable the injection of a medicine into the patient. The injection station includes a container 112 holding an injectant solution 114, a syringe 116 for pumping the injectant into the venous catheter, and a pair of check valves 118, 120 for controlling injectant flow. In order to inject the injectant solution, the clinician presses a button that causes an actuator 122 to move back the plunger on the syringe. This causes injectant to flow through valve 120 into the syringe. The actuator 122 then moves the syringe plunger forward to pump the fluid through valve 118 into the venous catheter. Since the volume of injectant may be small, it may not fill the venous catheter and initially enter the patient. However, after the syringe plunger is moved forward, the system initiates a flush cycle which causes saline solution to flow into the venous catheter and to the patient, to thereby carry the injectant medicine into the patient.

Figure 7:
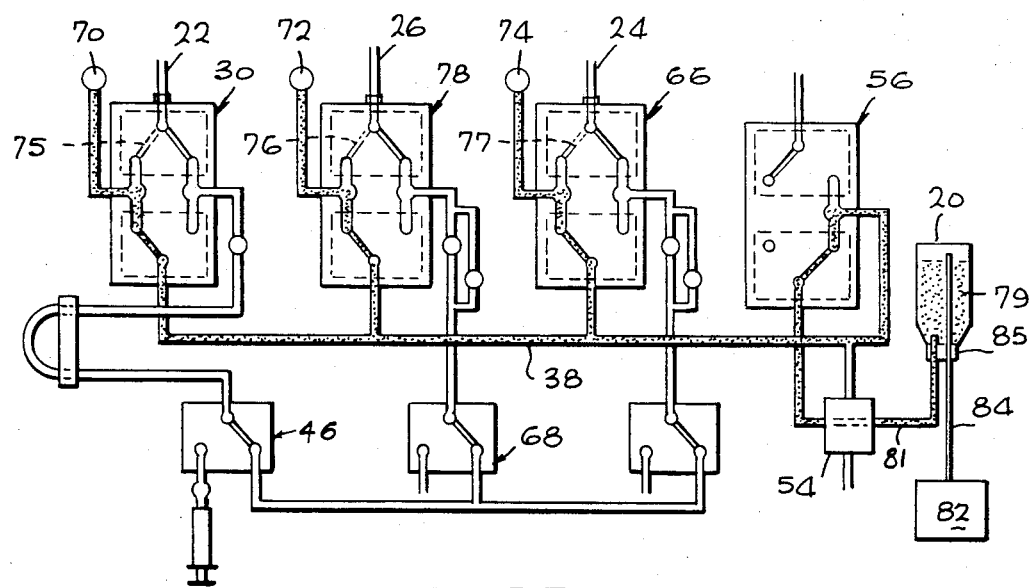
FIG. 7 is a diagram of the apparatus of FIG. 2, shown during the first step in a calibration process.

In between the taking of samples and other procedures, the apparatus is placed in a pressure monitoring state. As shown in FIG. 7, pressure transducers 70, 72, 74 can be coupled through valves to the arterial catheter 22, pulmonary artery catheter 26 and venous catheter 24, respectively, to indicate the pressures at corresponding points of the body. This is accomplished by the connections indicated in phantom lines at 75–77, which indicate the connections of the interface valves 30, 78, and 66. However, to provide accurate pressure indications, it is necessary to calibrate the transducers. This is accomplished by first calibrating the transducers 70–74 to a "o" pressure, and then to a high pressure such as 200 mmHg.

Calibration of the transducers can be accomplished as indicated in FIG. 7, by first utilizing the pressure applied by saline solution 79 in the bottle 20. The valves are adjusted so that fluid flows from the bottle 20 through a saline-carrying tube 81 to the flush block 54 and flush valve 56, through the flush manifold 38, which serves as a calibration line and through the interface valves 30, 78 and 66 to the corresponding transducers 70, 72, and 74. With the same low pressure applied to all of the transducers, they all can be adjusted to read "0". Following this, a higher pressure such as 200 mmHg is applied by a calibration pressure source 82 through a tube 84 that leads through a stopper 84 at the "bottom" of the bottle to the top of the bottle, to apply a high pressure to all of the transducers. This pressure can represent the top of the scale of the transducers, and when the pressure is applied the transducers can be adjusted to read 200 mmHg. By thus adjusting the transducers to all read the same at the bottom and top of their scales, a fair degree of relative accuracy can be obtained for the transducer readings which are between the top and bottom of scale.

In most cases, it is desirable to reference the pressure range to a point on the patient, instead of to the pressure applied by the saline solution in the bottle 20, which includes the pressure head of the solution as well as the ambient pressure. FIG. 8 illustrates interconnections that can be utilized to provide a patient reference calibration. The apparatus includes a patient calibration tube 83 which is filled with fluid and which has an end applied to the patient's midchest area, so that an pressure is applied to the end of the tube which represents the midchest pressure of the patient. This pressure is applied through the flush valves 56 to the flush manifold 38, so that the pressure is applied to each of the transducers 70, 72, 74, which can be calibrated to read "0" when the midchest pressure is applied.

FIG. 9 illustrates the construction of one of the valves of the apparatus, the particular valve 30 being the arterial interface valve. The valve 30 includes a stationary member 90 and a pair of movable members 92, 94 pivotably mounted about the axis 96 on the stationary member 90. The stationary member has two through holes 98, 100 each of which can be aligned with holes 102, 104 on the pivotal members 92, 94. In order to move the valve 30 to the conditions shown in FIG. 3, the pivotal member 92 is pivoted so its hole is at position 102a wherein it is aligned with the through hole 100 in the stationary member. Also, the other pivotal member 94 is left in a position where its hole 104 is aligned with the hole 98. This allows fluid to flow from port 28 to port 40 or from port 32 to port 36. The pivotal members 92, 94 are pivoted by air-operated actuators (not shown) which are fed air pulses from circuitry in a circuit portion 18 on the apparatus of FIG. 1. Operation of a corresponding button on the control panel 16 will cause all of the appropriate valves to shift to the required position, so that a clinician does not have to separately operate many valves. FIG. 3 shows a hydraulic circuit 18a of the circuit portion of the apparatus, which is connected by air lines 108–112 to various valves to properly position them for the first arterial sample step. However, in case of power failure, each of the valves can be manually operated by means of the clinician manually pivoting each of the valve members such as 92, 94 of the appropriate valves.

The various valves, tubes and the like that carry saline or blood that can enter the patient, are all mounted on a top deck 120 (FIGS. 1 and 2) of the valving portion 14 of the apparatus. This arrangement facilitates the sterilizing of the system to prevent cross contamination of patients. When a patient no longer must use the apparatus, the top deck 120 is removed from the rest of the apparatus by unscrewing three screws 122 that hold the deck to a support plate 124 at the top of the main frame 126 of the system. The deck portion below each air operated valve has a lower surface that seats on O-ring 128 (FIG. 9) extending about corresponding holes in the support plate 124, to simplify removal of the deck. After a top deck is removed, it and the rest of the valving portion thereon can be placed in a shallow tray where it is soaked in a disinfectant, rinsed, dried, and sealed in an airtight plastic bag and gas sterilized for future use. In the meantime, another top deck with the rest of a valving portion thereon can be installed on the main frame 126 of the system, by laying it on the support plate and installing the three screws 122.

Thus, the invention provides a system for performing procedures involving the vascular system of a patient in an intensive care environment, which reduces the separate steps that must be performed by a clinician, to thereby save time and reduce the chance of error. In one procedure for taking an arterial blood sample, removal of saline solution from the catheter and other conduits is achieved by first interconnecting the arterial and venous catheters to establish a blood flow and by interrupting the flow to direct blood into a syringe only after appreciable blood has passed by the sample station. Furthermore, complete flusing of the system into the patient can be accomplished after the sample is taken, so that none of the blood not taken into the syringe is wasted. The apparatus also provides a calibration system which enables rapid calibration of each pressure-measuring system to the same pressure level. A location on the particular patient, such as the midchest level, can be utilized as one of the pressure levels to which the pressure measuring systems are calibrated, so that all readings are relative to the patient reference pressure.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A vascular interface apparatus, for connection to a patient comprising:
   an arterial station including an arterial station valve with first, second, and third ports and an arterial catheter coupled to said first port for connection to an artery of the patient;
   a venous station including a venous catheter for connection to a vein of the patient;
   a sample station which includes a sample valve having first, second, and third ports and a valve member movable to connect said first port to said second or third ports, and a syringe receiver means at said third port for receiving a syringe means that can hold a blood sample;
   a first conduit coupling said second port of said arterial station valve to said first port of said sample valve;
   a second conduit coupling said second port of said sample valve to said venous station;
   means for operating said sample valve to interconnect said first and second sample valve ports to cause blood flow from an artery to a vein past said sample station, and to interconnect said first and third sample valve ports to enable the filling of a syringe means with a blood sample;
   a flushing source which includes a container of flushing solution coupled to said third port of said arterial station valve; and
   flushing means for operating said arterial station valve to connect said third port to said first port to flush said arterial catheter by passing flushing solution through it, and also to pass flushing solution through the first and second conduits and through the venous catheter to the patient.

2. The apparatus described in claim 1 including:
   an injection station coupled to an end of said venous catheter, including syringe means coupled to said catheter to introduce a medicine thereto, whereby when said operating means connects said third and second ports of said arterial valve to flush the second conduit and venous catheter, the introduced medicine is carried into the vein of the patient.

3. A vascular interface apparatus, comprising:

an arterial station which includes an arterial catheter for connection to an artery of the body;

a vaneous station which includes a venous catheter for connection to a vein of the body;

an arterial transducer coupled to said arterial station to measure the arterial blood pressure;

a venous transducer coupled to said venous station to measure the venous blood pressure;

a container holding saline solution;

valve and conduit means operable to connect said container to said arterial and venous stations and to the transducers coupled thereto while blocking the application of blood pressure to said transducers; and means for applying a controlled pressure to said container to pressurize the saline solution to a predetermined pressure, whereby to enable simultaneous calibration of the transducers to the same pressure while maintaining the sterility of the system.

4. A method for taking a blood sample from a patient comprising:

connecting an arterial catheter to an artery of the patient;

connecting a venous catheter to a vein of the patient;

flowing fluid including blood from said patient through said arterial catheter, into a first part of a valve and out of a second part of the valve so fluid flows through the valve, and through said venous catheter to the patient;

said catheters and valve initially containing a nonblood fluid;

allowing sufficient fluid flow through said catheters and valve for blood from the patient's artery to pass said valve, and thereafter connecting said valve to a blood sample-holding device and flowing blood entering said first valve port into said sample-holding device.

5. The method described in claim 4 including:

after flowing blood into said sample-holding device, flowing a flushing fluid through said valve and one of said catheters into the patient, and also through the other catheter into the patient, to fill the valve and catheters with said flushing fluid.

* * * * *